United States Patent

Kunimi et al.

Patent Number: 5,962,655
Date of Patent: Oct. 5, 1999

[54] MONOAZO COMPOUND AND AN INTERMEDIATE FOR A FIBER-REACTIVE DYE COMPOUND

[75] Inventors: Nobutaka Kunimi, Toyonaka; Shigeru Sasaki, Osaka; Kouji Toishi, Hannan; Atsushi Inoue, Toyonaka, all of Japan

[73] Assignee: Sumitomo Chemical Company, Limited, Osaka, Japan

[21] Appl. No.: 09/009,499

[22] Filed: Jan. 20, 1998

[30] Foreign Application Priority Data

Jan. 22, 1997 [JP] Japan .................................. 9-009550

[51] Int. Cl.⁶ .................. C09B 62/008; C09B 62/51; D06P 1/38
[52] U.S. Cl. .................. 534/605; 534/612; 534/634; 534/635; 534/638; 534/641; 534/642
[58] Field of Search .................. 534/605, 612, 534/634, 635, 638, 641, 642

[56] References Cited

U.S. PATENT DOCUMENTS

| | | | |
|---|---|---|---|
| 4,875,903 | 10/1989 | Pedrazzi | 534/605 X |
| 5,342,927 | 8/1994 | Reddig et al. | 534/634 X |
| 5,541,300 | 7/1996 | Bootz et al. | 534/605 |
| 5,591,834 | 1/1997 | Bootz et al. | 534/634 X |
| 5,760,193 | 6/1998 | Russ et al. | 534/634 X |

FOREIGN PATENT DOCUMENTS

| | | |
|---|---|---|
| 0717084 | 6/1996 | European Pat. Off. . |
| 57-89679 | 6/1982 | Japan . |

OTHER PUBLICATIONS

Copy of Search and Examination Report dated Feb. 12, 1999.

*Primary Examiner*—Fiona T. Powers
*Attorney, Agent, or Firm*—Stevens, Davis, Miller & Mosher, L.L.P.

[57] ABSTRACT

There is provided a monoazo compound which is useful as a reactive dye for dyeing or printing a fiber material in an orange to scarlet color; and intermediate compounds for producing the compound is provided; the monoazo compound being represented by the following formula (1):

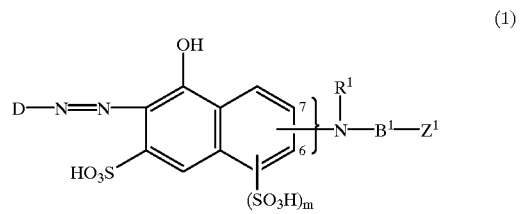

(1)

wherein m represents 0 or 1; $R^1$ represents a hydrogen atom or a lower alkyl group; D represents a specific diazo component of benzene type having substitution of a fiber reactive group; $B^1$ represents a direct bond or connecting group; $Z^1$ represents an alkylcarbonyl group, phenylcarbonyl group or a fiber-reactive group of vinylsulfone, triazine or pirimidine type; a group represented by —$NR^1$— bonds to 6-position or 7-position of a naphthalene ring;

and the intermediate compounds being represented by the following formulae (A) or (B):

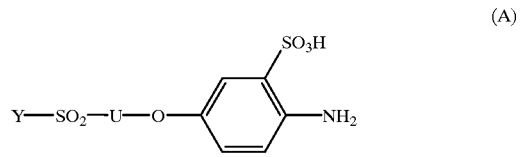

(A)

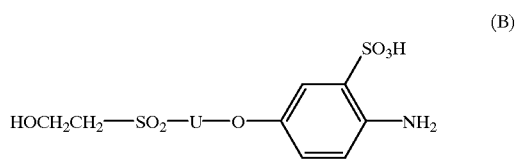

(B)

wherein U represents a connecting group such as alkylene and the like, Y represents vinyl or —$CH_2CH_2L$, and L represents a group eliminatable by an action of alkali.

14 Claims, No Drawings

MONOAZO COMPOUND AND AN INTERMEDIATE FOR A FIBER-REACTIVE DYE COMPOUND

The present invention relates to a fiber-reactive monoazo compound and an intermediate for producing a fiber-reactive dye compound.

The monoazo compound of the present invention is useful as an orange to scarlet reactive dye and suitable for dyeing an organic material having a hydroxyl group and/or an amide group, particularly cellulose fiber, natural or synthetic polyamide fiber, polyurethane finer, leather or the like or a mixed fiber containing any of them.

Further, the intermediate compound of the present invention can be used for production of a fiber-reactive dye compound.

Various reactive dyes are conventionally known and widely used in the field of dyeing and printing of a fiber material. For example, as a benzene-naphthalene-based monoazo compound which is an orange to scarlet reactive dye, there is known a monoazo compound represented by the following formula:

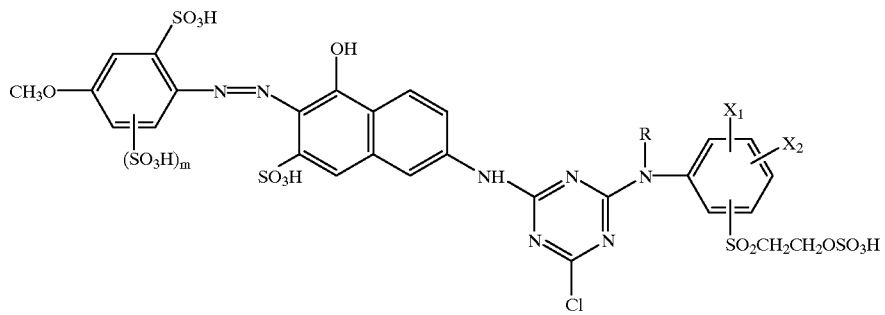

wherein R represents a lower alkyl group having up to 4 carbon atoms, $X_1$ and $X_2$ each independently represent a hydrogen atom, chlorine atom, methyl group, methoxy group or sulfonic acid group, and m represents 0 or 1, which has a fiber-reactive group of monochlorotriazine type via a —NH— group on the naphthalene ring side and further has a fiber-reactive group of vinylsulfone type which is substituted on a benzene group connected via a —NR— group to the monochlorotriazine ring.(JP-A-57-89679 etc.)

Further, a lot of compounds are conventionally known as an intermediate used for producing a reactive dye and the like.

The present inventors have intensely studied to develop a dye which provides an orange to scarlet dyed product or printed product which is better in reproducibility, leveling property and washing off property and has higher build-up property and dyeing ratio than conventional reactive dyes, and, further, can effect dyeing at low salt concentration, and is excellent in various fastness, in particular, chlorine fastness, light fastness, perspiration fastness, perspiration light fastness, acid hydrolysis fastness, alkali fastness, washing fastness and peroxide washing fastness in dyeing and printing treatment. As a result, it has been found that a specific benzene-naphthalene-based monoazo compound having a fiber-reactive group on the benzene ring side manifests intended abilities A novel intermediate which can be utilized for producing the compound has also been found. Thus, the present invention was completed.

The present invention provides a monoazo compound represented by the following general formula (1) or a salt thereof:

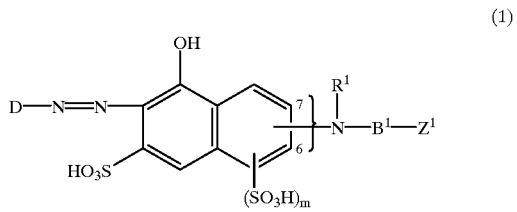

wherein, m represents 0 or 1, $R^1$ represents a hydrogen atom or a lower alkyl group which may be optionally substituted, D represents a group represented by the following general formula (2a), (2b) or (2c):

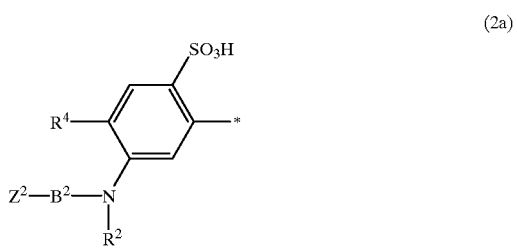

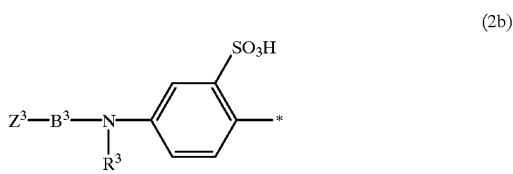

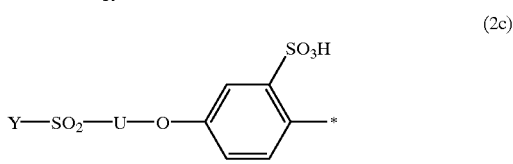

wherein $R^2$ and $R^3$ each independently represent a hydrogen atom or a lower alkyl group which may be optionally substituted, $R^4$ represents methyl or methoxy, U represent an alkylene which may be optionally interrupted by amino, carbamoyl, ureido or an oxygen atom, and * indicates a bond to an azo group, B$^1$, B$^2$ and B$^3$ each independently represent a direct bond or a connecting group represented by the following general formula (3):

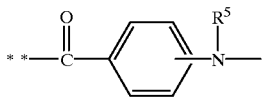
(3)

wherein, R$^5$ represents a hydrogen atom or a lower alkyl group which may be optionally substituted, ** indicates a bond to —NR$^1$—, —NR$^2$— or —NR$^3$—, Z$^1$ represents an alkylcarbonyl group which may be optionally substituted or a phenylcarbonyl group which may be optionally substituted, or a group represented by the following general formula (4a) or (4b), and Z$^2$ and Z$^3$ each independently represent a group represented by the following general formula (4a) or (4b):

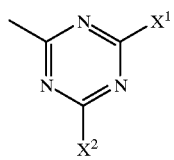
(4a)

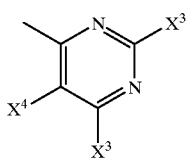
(4b)

wherein, both X$^1$ and X$^2$ represent chloro, or X$^1$ represents fluoro, chloro, pyridinio group which may be optionally substituted, or a group represented by the following formula (5a):

(5a)

and X$^2$ represents a group represented by the following general formula (5b), (5c), (5d) or (5e):

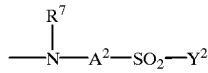
(5b)

(5c)

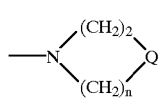
(5d)

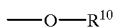
(5e)

wherein, A$^1$ and A$^2$ each independently represent alkylene which may be optionally substituted, phenylene which may be optionally substituted or naphthylene which may be optionally substituted, R$^6$, R$^7$, R$^8$, R$^9$ and R$^{10}$ each independently represent a hydrogen atom, alkyl which may be optionally substituted or phenyl which may be optionally substituted, Q represents —CH$_2$—, —O—, —S—, —SO$_2$— or —NR$^{11}$— wherein R$^{11}$ represents a hydrogen atom or alkyl which may be optionally substituted, n is 1, 2 or 3, X$^3$ represents fluoro or chloro, X$^4$ represents chloro, hydrogen atom, methyl or cyano, Y, Y$^1$ and Y$^2$ each independently represent —CH═CH$_2$ or —CH$_2$CH$_2$L wherein L represents a group which is eliminatable by the action of alkali, and a group represented by —NR$^1$ is linked to 6-position or 7-position of the naphthalene ring;

provided that, when D represents a group of the formula (2a) or (2b), B$^1$, B$^2$ and B$^3$ represent a direct bond, and Z$^1$, Z$^2$ and Z$^3$ represent a group represented by the general formula,(4a), then, the general formula (4a) represents a group represented by the following general formula (4a-1) or (4a-2):

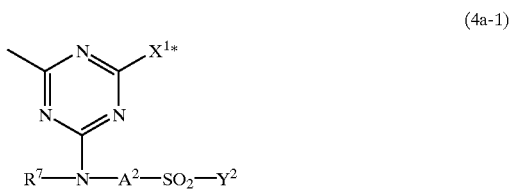
(4a-1)

(4a-2)

wherein, A$^1$, A$^2$, R$^6$, R$^7$, X$^2$, Y$^1$ and Y$^2$ are as defined above, X$^{1*}$ represents fluoro or chloro, X$^{2*}$ represents a group represented by the general formula (5b), (5c), (5d) or (5e) or a pyridinio group which may be optionally substituted, and Z$^1$ and Z$^2$ do not simultaneously represent the general formula (4a-1) and Z$^1$ and Z$^3$ do not simultaneously represent the general formula (4a-1);

and when D represents a group of the formula (2a) or (2b), B$^2$ and B$^3$ represent a direct bond, Z$^1$ represents an alkylcarbonyl group which may be optionally substituted or a phenylcarbonyl group which may be optionally substituted and B$^1$ represents a direct bond, then Z$^2$ and Z$^3$ represent a group represented by the general formula (4a-2).

The present invention also provides a method for dyeing or printing a fiber material using a monoazo compound represented by the general formula (1) or a salt thereof.

The present invention further provides an intermediate represented by the following general formula (A) and a salt thereof, and an intermediate compound represented by the following general formula (B) and a salt thereof:

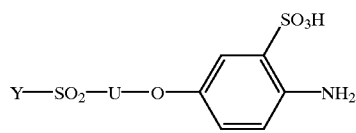

(A)

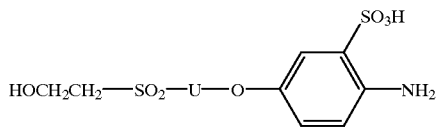

(B)

wherein U and Y are as defined above.

In the general formula (1), $R^1$ represents a hydrogen atom or a lower alkyl group which may be optionally substituted.

As examples of the lower alkyl group which may be optionally substituted, an alkyl group having 1 to 4 carbon atoms are listed. Examples of the substituent thereof include alkoxy having 1 to 4 carbon atoms, hydroxy, halogeno, carboxy, carbamoyl aalkoxycarbonyl, alkylcarbonyloxy, cyano, sulfo and sulfamoyl.

Specific examples of the lower alkyl group which may be optionally substituted represented by $R^1$ include methyl, ethyl, n-propyl, isopropyl, n-butyl, isobutyl, sec-butyl, 2-hyroxyethyl, 2-hydroxypropyl, 3-hyroxypropyl, 2-hydroxybutyl, 3-hydroxybutyl, 4-hydroxybutyl, 2,3-dihydroxypropyl, 3,4-dihydroxybutyl, cyanomethyl, 2-cyanoethyl, 3-cyanopropyl, methoxymethyl, ethoxymethyl, 2-methoxyethyl, 2-ethoxyethyl, 3-methoxypropyl, 3-ethoxypropyl, 2-hydroxy-3-methoxypropyl, chloromethyl, bromomethyl, 2-chloroethyl, 2-bromoethyl, 3-chloropropyl, 3-bromopropyl, 4-chlorobutyl, 4-bromobutyl, carboxymethyl, 2-carboxyethyl, 3-carboxypropyl, 4-carboxybutyl, 1,2-carboxyethyl, carbamoylmethyl, 2-carbamoylethyl, 3-carbamoylpropyl, 4-carbamoylbutyl, methoxycarbamoylmethyl, ethoxycarbonylmethyl, 2-methoxycarbamoyethyl, 2-ethoxycarbamoyethyl, 3-methoxycarbamoypropyl, 3-ethoxycarbonylpropyl, 4-methoxycarbonylbutyl, 4-ethoxycarbonylbutyl, methycarbonyloxyethyl, ethylcarbamoyoxymethyl, 2-methycarbonyloxyethyl, 2-ethylcarbonyloxyethyl, 3-methycarbonyloxypropyl, 3-ethycarbonyloxypropyl, 4-metylcarbonyloxybutyl, 4-ethylcarbonyloxybutyl, sulfometnyl, 2-sulfoethyl, 3-sulfopropyl, 4-sulfobutyl, sulfamoylmethyl, 2-sulfaomylethyl, 3-sulfamoylpropyl and 4-sulfamoylbutyl.

As $R^1$, a hydrogen atom or a lower alkyl group which is not substituted are preferred. Among them, hydrogen, methyl and ethyl are particularly preferred.

In the general formula (1), D represents a group represented by the general formula (2a), (2b) or (2c).

$R^2$ and $R^3$ in the general formulae (2a) and (2b) each independently represent a hydrogen atom or a lower alkyl group which may be optionally substituted. As examples of the lower alkyl group which may be optionally substituted, an alkyl group having 1 to 4 carbon atoms are listed. Examples of the substituent thereof include alkoxy having 1 to 4 carbon atoms, hvdroxy, halogeno, carboxy, carbamoyl, alkoxycarbonyl, alkylcarbonyloxy, cyano, sulfo and sulfamoyl. Specific examples of the lower alkyl group as $R^2$ or $R^3$ include the same groups as exemplified for $R^1$. As $R^2$ and $R^3$, a hydrogen atom or a lower alkyl group which is not substituted are preferred. Among them, a hydrogen atom, methyl and ethyl are particularly preferred.

$R^4$ in the general formula (2a) represents methyl or methoxy. Among them, methoxy is preferred.

U in the general formulae (2c), (A) and (B) represents an alkylene which may be optionally interrupted by amino, carbamoyl, ureido or an oxygen atom. Specific examples thereof include groups represented by the following groups:

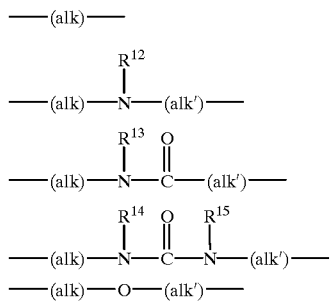

wherein (alk) and (alk') each independently represent alkylene having 1 to 6 carbon atoms, and $R^{12}$, $R^{13}$, $R^{14}$ and $R^{15}$ each independently represent a hydrogen atom or a lower alkyl. The alkylene group represented by (alk) or (alk') may be straight or branched, and preferably a straight alkylene. The group represented by $R^{12}$, $R^{13}$, $R^{14}$ or $R^{15}$ is preferably a hydrogen atom, methyl or ethyl. Either end of a divalent group represented by the formulae above may be linked to the O atom.

As U, a group represented by —(alk)— is preferred. Among them, alkylene having 3 to 6 carbon atoms is particularly preferred.

$B^1$, $B^2$ and $B^3$ in the general formulae (1), (2a) and (2b) each independently represent a direct bond or a connecting group represented by the general formula (3).

$R^5$ in the general formula (3) represents a hydrogen atom or a lower alkyl which may be optionally substituted. As examples of the lower alkyl group which may be optionally substituted, an alkyl group having 1 to 4 carbon atoms are listed. Examples of the substituent thereof include alkoxy having 1 to 4 carbon atoms, hydroxy, halogeno, carboxy, carbamoyl, alkoxycarbonyl, alkylcarbonyloxy, cyano, sulfo and sulfamoyl. Specific examples of the lower alkyl group as $R^5$ include the same groups as exemplified for $R^1$. As $R^5$, a hydrogen atom or a lower alkyl group which is not substituted are preferred. Among them, a hydrogen atom, methyl and ethyl are particularly preferred.

As $B^1$, $B^2$ and $B^3$ in the general formulae (1), (2a) and (2b), a direct bond is particularly preferred.

$Z^1$ in the general formula (1) represents an alkylcarbonyl group which may be optionally substituted, a phenylcarbonyl group which may be optionally substituted, and a group represented by the general formula (4a) or (4b). $Z^2$ and $Z^3$ in the general formulae (2a) and (2b) represent a group represented by the general formula (4a) or (4b). When both $Z^1$ and $Z^2$ or both $Z^1$ and $Z^3$ represent a group of general formula (4a) or (4b), they may be the same or different.

The alkyl moiety of the alkylcarbonyl group which may be optionally substituted usually has 1 to 4 carbon atoms. Examples of the substituent of the alkylcarbonyl group as $Z^1$ include an alkyl having 1 to 4 carbon atoms, alkoxy having 1 to 4 carbon atoms, hydroxy, halogeno, carboxy, carbamoyl, alkoxycarbonyl, alkylcarbonyloxy, cyano, sulfo and sulfamoyl.

As the alkylcarbonyl group as $Z^1$, an acetyl group, propionyl group, 2-carboxyethylcarbonyl group and 2-carboxyvinylcarbonyl group are preferred.

Examples the substituent of the phenylcarbonyl group which may be optionally substituted include an alkyl having 1 to 4 carbon atoms, alkoxy having 1 to 4 carbon atoms, hydroxy, halogeno, carboxy, carbamoyl, alkoxycarbonyl, alkylcarbonyloxy, cyano, sulfo and sulfamoyl.

As the phenylcarbonyl group as $Z^1$, a benzoyl group, 4-methylbenzoyl group and 4-methoxybenzoyl group are preferred.

Both $X^1$ and $X^2$ in the general formula (4a) may be chloro. Alternatively, $X^1$ represents fluoro, chloro, pyridinio which may be optionally substituted or a group represented by the general formula (5a), and $X^2$ represents a group represented by the general formula (5b), (5c), (5d) or (5e).

$X^{1*}$ in the general formula (4a-1) represents fluoro or chloro, $X^{2*}$ in the general formula (4a-2) represents a group represented by the general formula (5b), (5c), (5d) or (5e) or a pyridinio group which may be optionally substituted.

Examples of the pyridinio group which may be optionally substituted as $X^1$ or $X^{2*}$ include pyridinio, 2-, 3- or 4-carboxypyridio, 2-, 3- or 4-carbamoylpyridirio, 3-sulfopyridinio, 4-(2-sulfoethyl)pyridinio, 3-(2-hydroxyethyl)pyridinio, 4-chloropyridinio, 3-methylpyridinio and 3,5-dicarboxypyridinio. Among them, 3- or 4-carboxnylpyridinio are particularly preferred.

$R^6$, $R^7$, $R^8$, $R^9$ and $R^{10}$ in the general formulae (5a), (5b), (5c) and (5d) each independently represent a hydrogen atom, alkyl which may be optionally substituted or phenyl which may be optionally substituted.

Examples of the alkyl group which may be optionally substituted include alkyl having 1 to 4 carbon atoms and cyclohexyl, both of which may be optionally substituted with one or two substituents selected from the group consisting of alkoxy having 1 to 4 carbon atoms, sulfo, carboxy, sulfamoyl, carbamoyl, hydroxy, halogeno, cyano, carboxylate, sulfonate, phenyl which may be optionally substituted and sulfate. Examples of the phenyl which may be optionally substituted include phenyl which may be optionally substituted with one or two substituents selected from the group consisting of alkyl having 1 to 4 carbon atoms, alkoxy having 1 to 4 carbon atoms, sulfo and halogeno.

Specific examples of the alkyl which may be optionally substituted include the same groups as exemplified for $R^1$, and benzyl which may be optionally substituted, in addition. Among them, methyl, ethyl, n-propyl, isopropyl, n-butyl, isobutyl, sec-butyl, 2-hydroxyethyl, 2-sulfoethyl, 2-methoxyethyl, 2-carboxyethyl, 2-carbamoylethyl, 2-sulfamoylethyl, benzyl or 2-, 3- or 4-sulfobenzyl are preferred.

Examples of the phenyl group which may be optionally substituted, as $R^6$, $R^7$, $R^8$, $R^9$ and $R^{10}$, include phenyl which may be optionally substituted with one or two substituents selected from the group consisting of alkyl having 1 to 4 carbon atoms, alkoxy having 1 to 4 carbon atoms, sulfo, carboxy, halogeno, hydroxy, cyano, carbamoyl, sulfamoyl, carboxylate, 2-hydroxyethysulfonyl, amino, acylamino, and amino substituted with alkyl having 1 to 4 carbon atoms.

Specific examples of the phenyl which may be optionally substituted include phenyl, 2-, 3- or 4-methylphenyl, 2-, 3- or 4-methoxyphenyl, 2-, 3- or 4-ethylphenyl, 2-, 3- or 4-ethoxyphenyl, 2-, 3- or 4-isopropylphenyl, 2-, 3- or 4-carboxyphenyl, 2-, 3- or 4-carbamoylphenyl, 2-, 3- or 4-chlorophenyl, 2-, 3- or 4-sulfophenyl, 2-, 3- or 4-hydroxyphenyl, 2-sulfo-4-methoxyphenyl, 2-sulfo-4-acetylaminophenyl, 2-carboxy-4-acetylaminophenyl, 2-methoxy-5-methyphenyl, 2,4-dimethoxyphenyl and 2,5-dimethoxyphenyl.

As $R^6$ and $R^7$, a hydrogen atom or a lower alkyl group which is not substituted are preferred. Among them, methyl and ethyl are particularly preferred.

Regarding $R^8$ and $R^9$, it is preferred that one or them is a hydrogen atom or alkyl which may be optionally substituted, and the other is phenyl which may be optionally substituted. More preferably, $R^8$ represents a hydrogen atom, methyl or ethyl, and $R^9$ represents phenyl which may be optionally substituted by a group selected from the group consisting of alkyl having 1 to 4 carbon atoms, alkoxy having 1 to 4 carbon atoms, sulfo, carboxy, halogeno, hydroxy, cyano and acylamino.

Example of an amine compound represented by $NHR^8R^9$ which is used to form the group represented by the general formula (5c) include:

Ammonia;

Aromatic amines such as 1-aminobenzene, 1-amino-2-, -3- or -4-methylbenzene, 1-amino-2,4-, -3,4- or -3,5-dimethylbenzene, 1-amino-2-, -3- or -4-ethylbenzene, 1-amino-2-, -3- or -4-methoxybenzene, 1-amino-2-, -3- or -4-ethoxybenzene, 1-amino-2-, -3- or -4-proplbenzene, 1-amino-2-, -3- or -4-isopropylbenzene, 1-amino-2-, -3- or -4-chlorobenzene, 1-amino-2-, -3- or-4-bromobenzene, 1-amino-2-, -3- or-4-fluorobenzene, 1-amino-2,4- or -2,5-dimethoxybenzene, 1-amino-2-methoxy-5-methylbenzene, 3- or 4-aminophenylmethanesulfonic acid, 2-, 3- or 4-aminobenzenesulfonic acid, 3- or 4-methylaminobenzenesulfonic acid, 3- or 4-ethylaminobenzenesulfonic acid, 5-aminobenzene-1,3-disulfonic acid, 6-aminobenzene-1,3- or -1,4-disulfonic acid, 4-aminobenzene-1,2-disulfonic acid, 4-amino-5-methylbenzene-1,2-disulfonic acid, 1-amino-2-sulfo-4-methoxybenzene, 1-amino-2-sulfo-4-acetylaminobenzene, 2-, 3- or 4-aminobenzoic acid, 2-, 3- or 4-carbamoylaniline, 1-amino-2-carboxy-4-acetylaminobenzene, 5-aminobenzene-1,3-dicarboxylic acid, 5-amino-2-hydroxybenzenesulfonic acid, 4-amino-2-hydroxybenzenesulfonic acid, 5-amino-2-ethoxybenzenesulfonic acid, N-methylaminobenzene, N-ethylaminobenzene, 1-methylamino-3- or-4-methylbenzene, 1-ethylamino-3- or -4-methylbenzene, 1-methylamino-2-, -3- or -4-chlorobenzene, 1-ethylamino-2-, -3- or -4-chlorobenzene, 1-2-hydroxyethyl) amino-3-methylbenzene, 3- or 4-methylaminobenzoic acid, 1-amino-2-methoxy-5-methylbenzene, 1-amino-2,5-dimethoxybenzene, 2-, 3- or 4-aminophenol, 1-amino-3- or -4-acetylaminobenzene, 2,4- or 2,5-diaminobenzenesulfonic acid, and 1-aminobenzene-3- or -4(β-hydroxyethylsulfone);

Aliphatic amines such as methylamine, ethylamine, n-propylamine, isopropylamine, n-butylamine, isobutylamine, sec-butylamine, dimethylamine, diethylamine, methylethylamine, allylamine, 2-cloroethylamine, 2-methoxyethylamine, 2-aminoethanol, 2-methylaminoethanol, bis(2-hydoxyethyl)amine, 2-aceytlaminoethylamine, 1-amino-2-propanol, 3-methoxypropylamine, 1-amino-3-dimethylaminopropane, 2-aminoethanesulfonamide, 2-aminoethanesulfonic acid, aminomethanesulfonic acid, 2-methylaminoethanesulfonamide, 2-methylaminoethanesulfonic acid, 3-amino-1-propanesulfonic acid, 2-sulfate ethylamine, aminoacetic acid, methylaminoacetic acid, 3-aminopropionic acid, 3-aminopropionamide, 3-methylaminopropionamide, ε-aminocapronic acid, benzylamine, 2-, 3- or 4-sulfobenzylamine, 2-, 3- or 4-chlorobenzylamine, 2-, 3- or 4-methylbenzylamine, N-methybenzylamine, 1-phenylethylamine, 2-phenylethylamine, and 1-phenyl-2-propylamine.

Preferred examples of the amine compound include aniline, N-methylaniline, N-ethylaniline, 2-, 3- or 4-chloroaniline, N-methyl-2-, -3- or -4-chloroaniline, N-ethyl-2-, -3- or -4-chloroaniline, 2-, 3- or 4-methylaniline, 2-, 3- or 4-ethylaniline, 2-, 3- or 4-methoxyaniline, 2-, 3- or 4-ethoxyaniline, 2-, 3- or 4-propylaniline, 2-, 3- or 4-isopropylaniline, 2-, 3- or 4-hydroxyaniline, aniline-2-, -3- or-4-sulfonic acid, 3- or 4-methylaminobenzenesulfonic acid, 3- or 4-ethylaminobenzenesulfonic acid, 2-3- or 4-carboxyaniline, 2-, 3- or 4-carbamoylaniline, 2,4- or 2,5-dimethoxyaniline, 2-sulfo-4-methoxyaniline, 2-sulfo-4-acetylaminoaniline, 2-carboxy-4-acetylaminoaniline, 2-methoxy-5-methylaniline, ammonia, methylamine, ethylamine, dimethylamnine, taurine, N-methyltaurine, mono- or diethanolamine, 2-sulfamoylethylamine, and 2-carbamoylethylamine.

Among them, aniline, N-methylaniline, N-ethylaniline, N-ethyl-2-, -3- or -4-chloroaniline, 2-, 3- or 4-ethylaniline, 2-, 3- or 4-methoxyaniline, 2-, 3- or 4-propylaniline, 2-, 3- or 4-isopropylaniline, 2-, 3- or 4-hydroxyaniline, aniline-2-, -3- or -4-sulfonic acid, 2-, 3- or 4-carboxyaniline, 2-, 3- or 4-carbamoylaniline, 2,4- or 2,5-dimethoxyaniline, 2-sulfo-4-methoxyaniline, 2-sulfo-4-acetylaminoaniline, 2-carboxy-4-acetylaminoaniline, 2-methoxy-5-methyaniline are particularly preferred.

Example of a hydroxy compound represented by $HOR^{10}$ which is used to form the group represented by the general formula (5e) include:

Phenols such as phenol, 1-hydroxy-2-, -3- or -4-methylbenzene, 1-hydroxy-3,4- or -3,5-diemthylbenzene, 1-hydroxy-2-, -3- or -4-ethylbenzene, 1-hydroxy-2-, -3- or -4-methoxybenzene, 1-hydroxy-2-, -3- or -4-ethoxybenzene, 1-hydroxy-2-, -3- or -4-chlorobenzene, 3- or 4-hydroxyphenylmethanesulfonic acid, 3- or 4-hydroxybenzenesulfonic acid, 5-hydroxybenzene-1,3-disulfonic acid, 2-hydroxybenzene-1,4-disulfonic acid, 4-hydroxybenzene-1,2-disulfonic acid, 4-hydroxy-5-methylbenzene-1,2-disulfonic acid, 3- or 4-hydroxybenzoic acid, 5-hydroxybenzene-1,3-dicarboxylic acid, and 5-hydroxy-2-ethoxybenzenesulfonic acid;

Aliphatic alcohols such as methanol, ethanol, n-propanol, isopropanol, n-butanol, isobutanol, sec-butanol, 2-chloroethanol, 2-methoxyethanol, 2-ethoxyethanol, 3-methoxypropanol, 3-ethoxypropanol, 2-hydroxyethaneuslfonic acid, 3-hydroxyethoxypropanol, 3-hydroxy-1-propanesulfonic acid, 2-cyanoethanol, 2-sulfateethanol, glycolic acid, 3-hydroxypropionic acid, benzyl alcohol, 2-, 3- or 4-chlorobenzyl alcohol, 4-methylbenzyl alcohol, 2-, 3- or 4-sulfobenzyl alcohol, 2-phenylethanol and 1-phenyl-2-propanol.

In the general formula (5d), Q represents —$CH_2$—, —O—, —S—, —$SO_2$— or —$NR^{11}$— wherein, $R^{11}$ represents hydrogen or alkyl which may be optionally substituted, and n represents 1, 2 or 3. Examples of the group represented by $R^{11}$ include a hydrogen atom and alkyl having 1 to 4 carbon atoms Among them, a hydrogen atom, methyl and ethyl are particularly preferred. Specific examples of the group represented by the general formula (5d) include residues derived from pyrrolidine, piperidine, piperazine, n-alkylpiperazine and morpholine. Among them, the group of formula (5d) wherein n is 2 and Q is —O— or —$CH_2$—, that is morpholino or piperidino, is particularly preferred.

$A^1$ and $A^2$ in the general formulae (5a) and (5b) each independently represent alkylene, phenylene which may be optionally substituted, or naphthylene which may be optionally substituted.

Examples of the alkylene which may be optionally substituted and is represented by $A^1$ or $A^2$ include alkylene which has 2 to 4 carbon atoms and may be substituted with a substituent selected from the group consisting of alkyl having 1 to 4 carbon atoms, halogeno, hydroxy, sulfo, cyano, alkoxy having 1 to 4 carbon atoms, alkoxycarbonyl having 1 to 4 carbon atoms, alkylcarbonyloxy having 1 to 4 carbon atoms and carbamoyl. Among them, unsubstituted alkylene having 2 to 4 carbon atoms, particularly ethylene and trimethylene, are preferred.

Preferable examples of the phenylene which may be optionally substituted and is represented by $A^1$ or $A^2$ include unsubstituted phenylene and phenylene substituted with one or two substituents selected from the group consisting of alkyl having 1 to 4 carbon atoms, alkoxy having 1 to 4 carbon atoms, sulfo and halogeno (chloro, bromo and the like). Among them, unsubstituted phenylene and phenylene substituted with one or two substituents selected from the group consisting of methyl, ethyl, methoxy, ethoxy, chloro, bromo and sulfo is particularly preferable. Examples of the phenylene represented by $A^1$ or $A^2$ include the following groups:

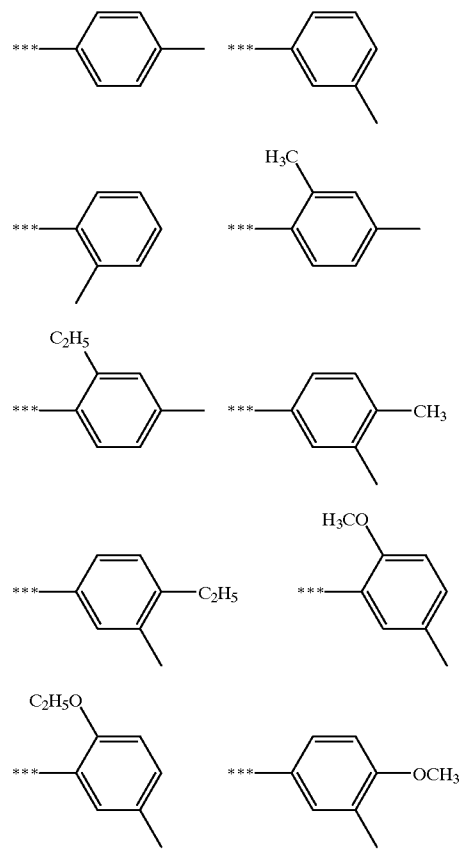

-continued

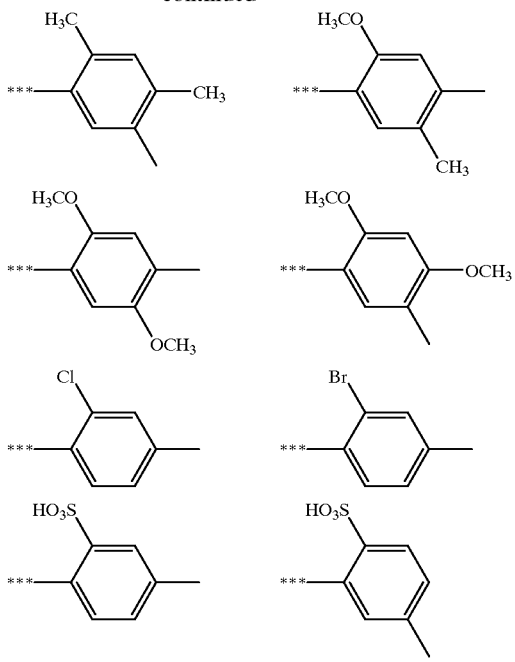

wherein *** indicates a bond to —NR⁶— or —NR⁷—. Among them, unsubstituted phenylene and phenylene substituted with one or two groups selected from methyl or methoxy are particularly preferred.

Preferable examples of the naphthylene which may be substituted and is represented by $A^1$ or $A^2$ include unsubstituted naphthylene and naphthylene substituted with one or two sulfo groups. Examples of the naphthylene represented by $A^1$ or $A^2$ include the following groups:

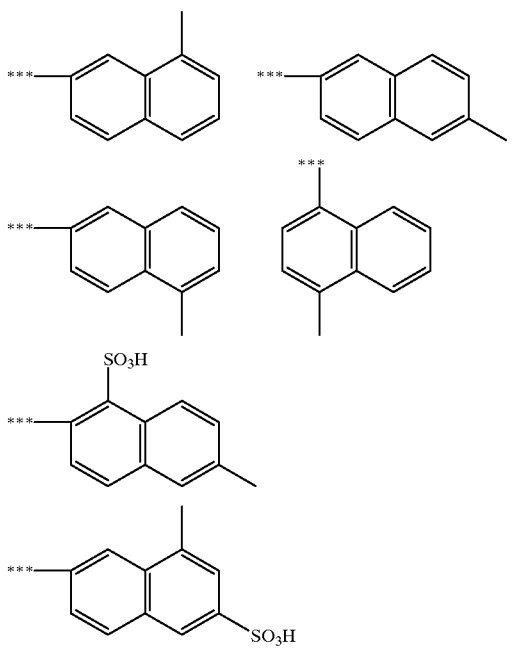

-continued

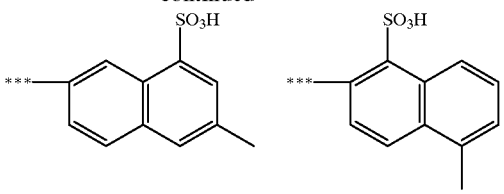

wherein ***indicates a bond to —NR⁶— or —NR⁷—.

Preferable examples of the group represented by the general formula (4a) include the following groups:

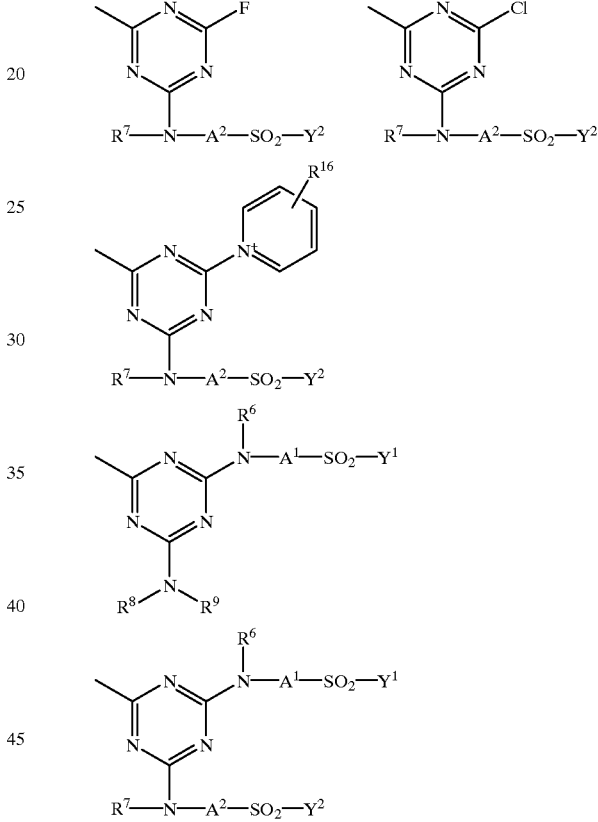

wherein $A^1$, $A^2$, $R^6$, $R^7$, $R^8$, $R^9$, $Y^1$ and $Y^2$ are as defined above, and $R^{16}$ represents a carboxyl group or carbamoyl group.

In the general formula (4b), $X^3$ represents fluoro or chloro, and $X^4$ represents chloro, hydrogen atom, methyl or cyano. Specific examples of the group represented by the general formula (4b) include the following groups:

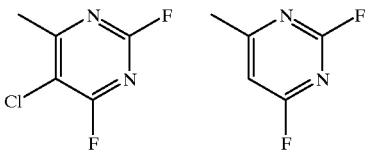

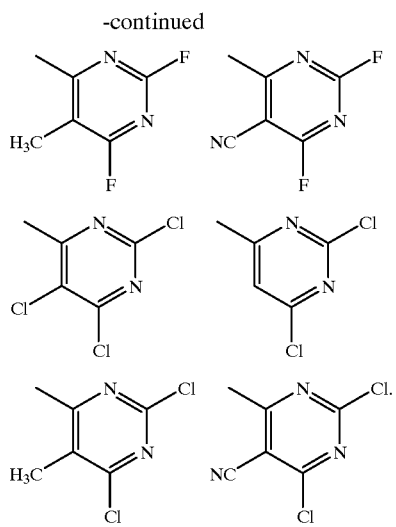

Among them, difluoromonochloropyrimidinyl group and the like are particularly preferred.

In the formulae (2c), (5a), (5b), and (A), Y, $Y^1$ and $Y^2$ each independently represent —CH=CH$_2$— or —CH$_2$CH$_2$L, wherein L represents a group eliminatable by an action of alkali. Specific examples of L include sulfate, thiosulfate, phosphate, acetate and halogeno. Among them, sulfate and chloro are preferred.

Therefore, preferable examples of $Y^1$ and $Y^2$ include —CH=CH$_2$, —CH$_2$CH$_2$Cl and —CH$_2$CH$_2$OSO$_3$H, and —CH$_2$CH$_2$OSO$_3$H is particularly preferred.

The monoazo compound of the present invention and the intermediate compound of the present invention may be in the form of a free acid, i.e. the compound represented by the formula (1), (A) or (B), salt thereof, or mixture thereof. An alkaline metal salt thereof, alkali earth metal salt thereof and mixture containing them are preferred. Among them, sodium salt, potassium sale, lithium salt thereof and mixture containing them are particularly preferred.

When D in the formula (1) represents (2a) or (2b), $Z^2$ and $Z^3$ preferably represent (4a). Particularly preferable examples of the monoazo compound of the formula (1) wherein D represents (2a) or (2b) include the following compounds:

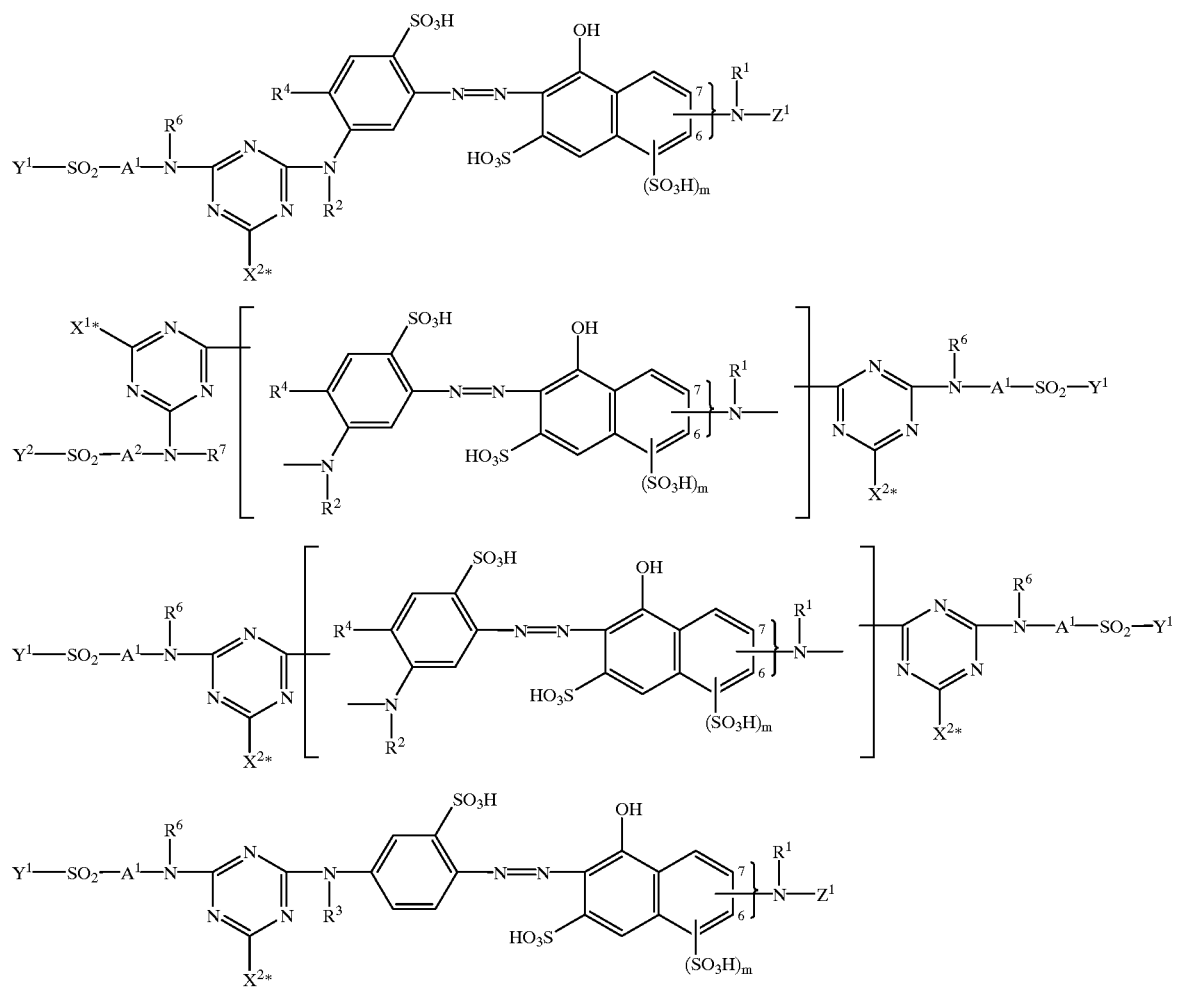

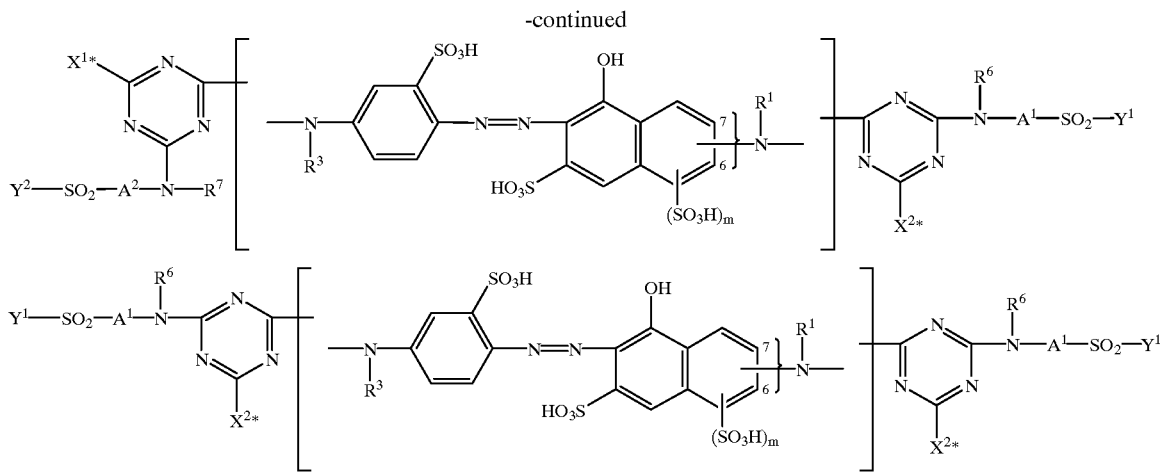

wherein $R^1, R^2, R^3, R^4, R^6, R^7, X^{1*}, X^{2*}, A^1, A^2, Y^1, Y^2$ and m are as defined above, and if one molecule has two $R^6$, $X^{2*}$, $A^1$ or $Y^1$, both of the groups may be the same or different each other.

Preferable examples of the monoazo compound of the formula (1) wherein D is (2c) include the following compounds:

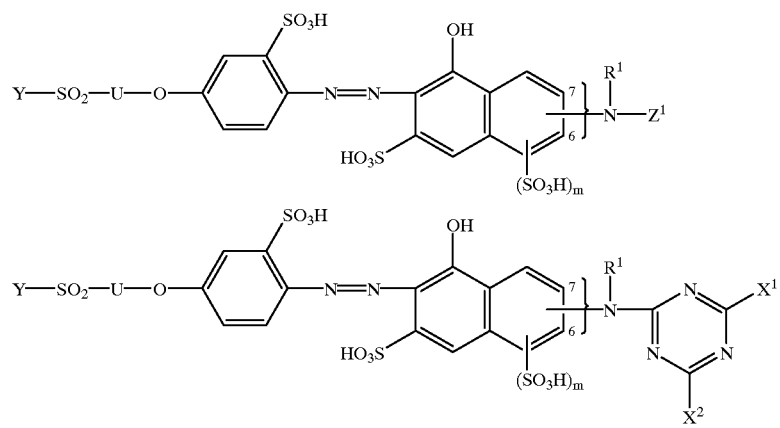

wherein $R^1$, $Z^1$, $X^1$, $X^2$, U, Y and m are as defined above.

Particularly preferable examples of the monoazo compound of the formula (1) include the following compounds:

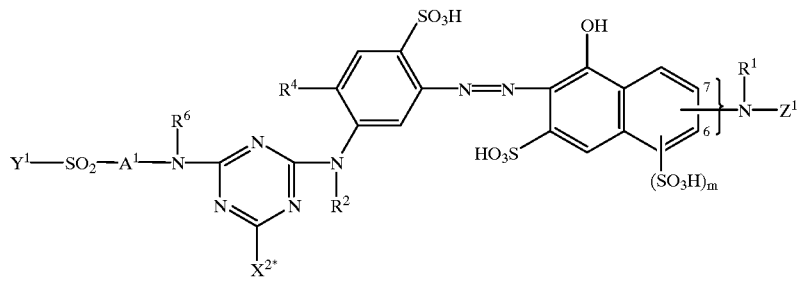

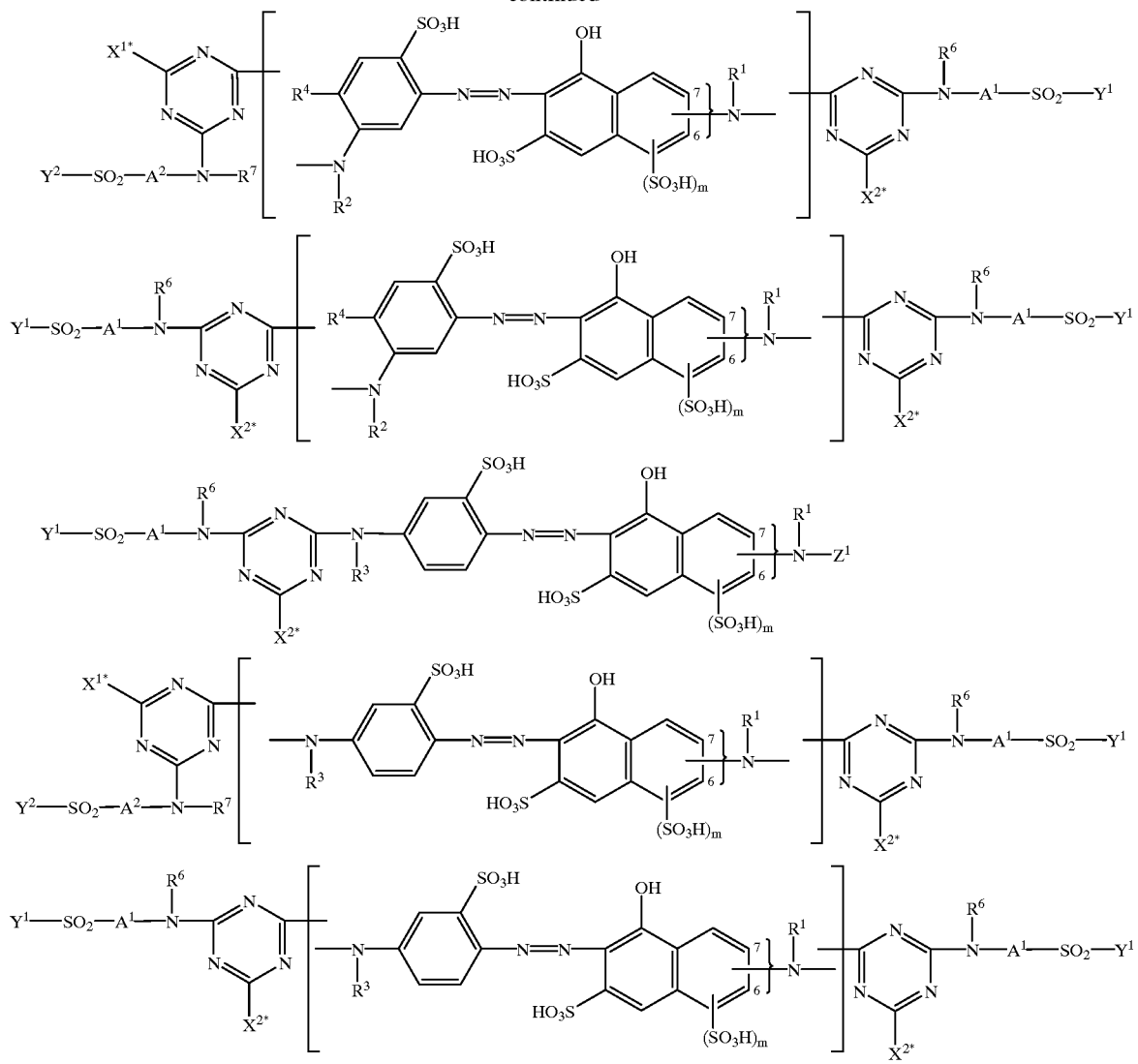

wherein $R^1$, $R^2$, $R^3$, $R^6$ and $R^7$ each independently represent a hydrogen atom, methyl or ethyl, $X^{2*}$ represents a group of the general formulae (5b) or (5c) or pyridinio which may be optionally substituted, $A^1$ and $A^2$ each independently represent ethylene, trimethylene or phenylene which may be optionally substituted, and $Y^1$, $Y^2$ and Y represent —CH$_2$CH$_2$OSO$_3$H;

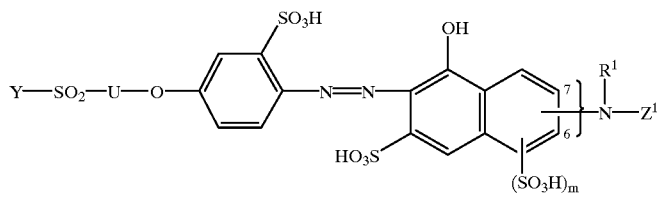

wherein $R^1$, $R^2$, $R^3$, $R^6$ and $R^7$ each independently represent a hydrogen atom, methyl or ethyl, $Z^1$ represents an alkylcarbonyl group which may be optionally substituted or aphenylcarbonyl group which may be optionally substituted, and U represents alkylene having 3 to 6 carbon atoms; and

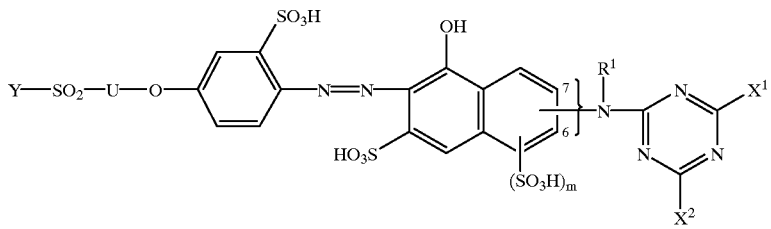

wherein $R^1$, $R^2$, $R^3$, $R^6$ and $R^7$ each independently represent a hydrogen atom, methyl or ethyl, $X^1$ represents fluoro, chloro or pridinio which may be optionally substituted and $X^2$ represents the general formula (5b), or $X^1$ represents the general formula (5a) and $X^2$ represents the general formula (5b) or (5c), and U represents alkylene having 3 to 6 carbon atoms.

Preferable examples the intermediate compound of the present invention represented by the general formula (A) include the group represented by the following formula:

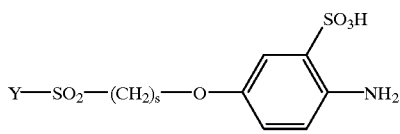

wherein s is from 3 to 6, and Y is as defined above.

Among them, a compound of the above formula in which Y represents —CH=CH—, —CH$_2$CH$_2$Cl or —CH$_2$CH$_2$OSO$_3$H is particularly preferred.

Preferable examples the intermediate compound of the present invention represented by the general formula (B) include the group represented by the following formula:

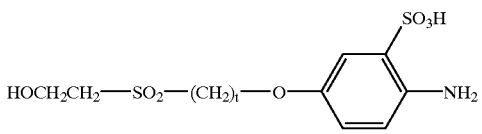

wherein t is from 3 to 6.

The production method for the monoazo compound (1) of the present invention is not particularly restricted. The monoazo compound (1) can be produced according to a known method. Examples of the production method include the following method.

Any of compounds of which free acids are represented. respectively by the following formulae (6a), (6b) and (A):

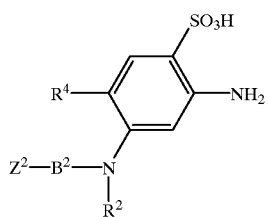

(6a)

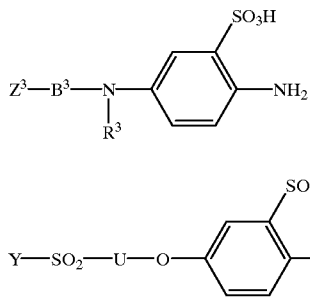

(6b)

(A)

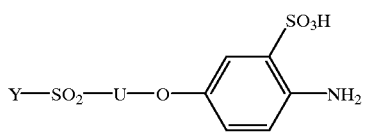

wherein, $R^2$, $R^3$, $R^4$, $B^2$, $B^3$, $Z^2$, $Z^3$, U and Y are as defined above is diazotized according to a conventional method. The resulted diazo compound is subjected to a coupling reaction according to a conventional method with a compound of which free acid is represented by the following formula (7):

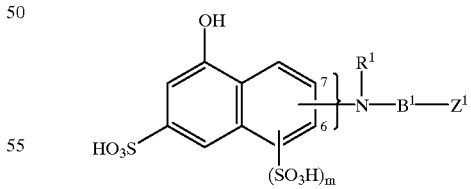

(7)

wherein, $R^1$, $B^1$, $Z^1$ and m are as defined above to produce the monoazo compound (1) of the present invention.

The compounds represented by the general formulae (6a), (6b) and (7) can also be produced by a known method. The compound represented by the general formula (6a) can be produced, for example, by a conventional condensation reaction of a compound of which free acid is represented by the following general formula (8a):

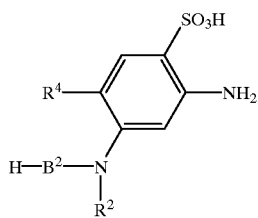 (8a)

wherein, $R^2$, $R^4$ and $B^2$ are as defined above with a compound represented by the following general formula (10a):

 $Z^2$—X  (10a)

wherein $Z^2$ is as defined above, and x represents halogeno such as fluoro and chloro.

The compound represented by the general formula (6b) can be produced, for example, by a conventional condensation reaction of a compound of which free acid is represented by the following general formula (8b):

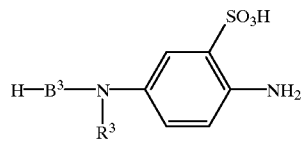 (8b)

wherein $R^3$ and $B^3$ are as defined above with a compound represented by the following general formula (10b):

 $Z^3$—X  (10b)

wherein, $Z^3$ is as defined above, and X represents halogeno such as fluoro and chloro.

The compound represented by the general formula (7) can be produced, for example, by a conventional condensation reaction of a compound of which free acid is represented by the following general formula (9):

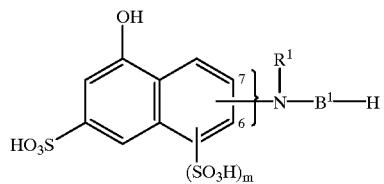 (9)

wherein $R^1$, $B^1$ and m are as defined above with a compound represented by the following general formula (10c):

 $Z^1$—X  (10c)

wherein, $Z^1$ is as defined above, and X represents halogeno such as flluoro and chloro.

When the monoazo compound (1) of the present invention contains at least any one of Y, $Y^1$ and $Y^2$, the Y, $Y^1$ or $Y^2$ represent —$CH_2CH_2L$, and the group L is an ester such as a sulfate ester, then, formation of the ester group may be conducted after the above-described coupling reactions and condensation reactions.

For example, when Y represents —$CH_2CH_2L$, and the group L is an ester such as a sulfate ester, it is possible that the coupling reaction as described above is conducted using a compound in which Y represents —$CH_2CH_2OH$, namely a compound represented by the general formula (B) instead of a compound represented by the general formula (A), followed by the esterification according to a known method, to obtain the compound When $Y^1$ and $Y^2$ represent —$CH_2CH_2L$, and the group L is an ester such as a sulfate ester, the same process as mentioned above can be effected.

The production method for the intermediate compound (A) of the present invention is not particularly restricted. It can be produced, for example, by using the intermediate compound (B) of the present invention. Namely, when Y represent —$CH_2CH_2L$, then, the compound (A) can be produced by effecting esterification or halogenoation, depending on the kind of the group L. The resulted compound can be subjected to a further alkali treatment for vinylation to produce the compound (A) wherein Y represents —CH=$CH_2$—. These esterification, halogenoation and elimination can be effected according to known methods respectively.

The production method of the intermediate compound (3) of the present invention is also not restricted. For example, the intermediate compound (B) can be produced by halogenating a compound represented by the following general formula (11);

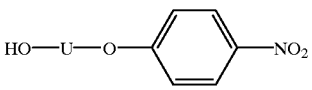 (11)

wherein U is as defined above to obtain a compound represented by the following general formula (12):

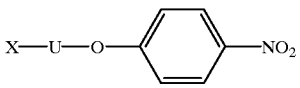 (12)

wherein U is as defined above, and X represents halogeno such as fluoro and chloro, condensing the resulted compound with mercaptoethanol according to a normal method to obtain a sulfide compound, subsequently oxidizing the sulfide compound to sulfone, then reducing the nitro group to an amino group, and sulfonating the aromatic ring. Here, the above-described respective unit reactions, namely, the condensing reaction, oxidizing reaction, reducing reaction and sulfonating reaction can be conducted according to known methods respectively.

The production method of the raw material compound (11) is not particularly restricted. The following methods can be exemplified.

1. When the compound (11) is

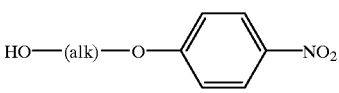 (11a)

wherein (alk) is as defined above, it can be produced, for example, by a conventional condensation of a compound represented by the following general formula (13a):

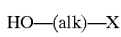 HO—(alk)—X  (13a)

wherein, (alk) is as defined above, and X represents halogeno such as fluoro and chloro with p-nitrophenol.

2. When the compound (11) is

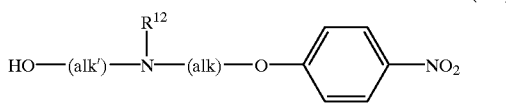
(11b)

wherein (alk), (alk') and $R^{12}$ are as defined above, t can be produced, for example, by halogenoation according to a known method of the compound represented by the general formula (11a), then by condensation according to a known method of the resulted compound with a compound represented by the following general formula:

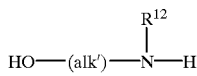
(13b)

wherein (alk') is as defined above.

3. When the compound (11) is

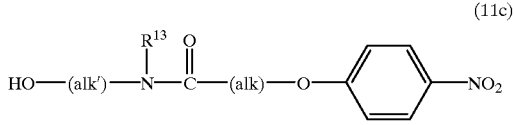
(11c)

wherein (alk), (alk') and $R^{13}$ are as defined above, it can be produced, for example, by condensation according to a known method of a compound represented by the following general formula:

(13-c-1)

wherein (alk) is as defined above, and X represents halogeno such as fluoro and chloro with p-nitrophenol, then by converting the condensate into an acid halide according to a known method, and further by condensing the resulted compound with a compound represented by the following general formula (13c-2):

(13c-2)

wherein (alk') and $R^{13}$ are as defined above according to a known method.

4. When the compound (11) is

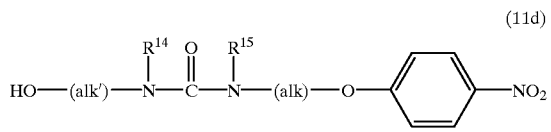
(11d)

wherein (alk), (alk') and $R^{13}$ are as defined above, it can be produced, for example, by condensation according to a known method of a condensation product of p-nitrophenol with a compound represented by the following general formula (13d-1):

(13d-1)

wherein (alk) and $R^{15}$ are as defined above, and X represents halogeno such as fluoro and chloro with a compound represented by the following general formula (13d-2)

(13d-2)

wherein (alk') and $R^{14}$ are as defined above, for example, using a ureido connecting agent such as phosgene 5. When the compound (11) is

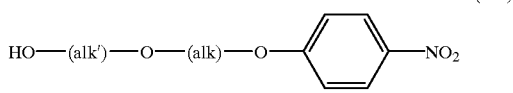
(11e)

wherein (alk) and (alk') are as defined above, it can be produced, for example, by halogenoation according to a known method of the compound represented by the general formula (11a), then by condensation according to a known method of the resulted compound with a compound represented by the following general formula (13e):

HO—(alk')—X       (13e)

wherein (alk') is as defined above, and X represents halogeno such as fluoro and chloro.

The monoazo compound (1) of the present invention has fiber-reactivity, and can be used for dyeing and printing of a hydroxyl group-containing or carbonamide group-containing material. It is preferable that the material is used in the form of a fiber material or mixed fiber material thereof.

Examples of the hydroxyl group-containing material include natural or synthetic hydroxyl group-containing materials, such as a cellulose fiber material or regeneration product thereof and polyvinyl alcohol. As the cellulose fiber material, cotton or other vegetable fiber such as linen, hemp, jute and ramie fiber are preferable. Examples of the reproduction cellulose fiber material include viscose staple and filament viscose.

Examples of the carbonamide group-containing material include synthetic or natural polyamide, polyurethane and leather. In particular, materials in the form of fiber, such as wool, hair of other animals, silk, polyamide-6,6, polyamide-6, polyamide-11 and polyamide-4 are preferable.

The monoazo compound (1) of the present invention can be used for dyeing or printing on the above-described materials, particularly the above-described fiber materials according to a method corresponding to their physicochemical properties.

For example, when the monoazo compound is exhausted on a cellulose fiber material for dyeing, it is conducted in he presence of an acid-bonding agent such as sodium carbonate, sodium tertiary phosphate and sodium hydroxide, optionally with adding a neutral salt such as sodium sulfate or sodium chloride, and if necessary, using a dissolution auxiliary, a penetrant or a leveling agent, at relatively low temperature. The neutral salt which promotes exhaustion of a dye can be added either after or before reaching the essential dyeing temperature. It may be added in portions.

When a cellulose fiber material is dyed according to a padding method, the padding is conducted at room temperature or elevated temperature. After drying, fixing can be effected by steaming or dry heating.

Printing on a cellulose fiber material can be carried out by applying a printing paste, such as those containing sodium hydrogen carbonate and other acid bonding agent, on the fiber material, then by conducting steaming at 95 to 160° C. (one-phase), or by applying a neutral or weak acidic printing paste on the fiber material, and passing this through a hot alkaline bath containing an electrolyte, or conducting overpadding with a padding solution containing an alkaline electrolyte, then effecting steaming or dry heating treatment. (two-phase)

For the printing paste, a pasting agent or an emulsifying agent such as sodium alginate and starch ether is used. Optionally, a usual printing auxiliary such as urea and/or a dispersing agent may be used together.

An acid bonding agent suitable for fixing the monoazo compound (1) of the present invention on cellulose fiber can be, for example, a hydroxide of alkaline metal, a water-soluble basic salt of alkaline metal or alkaline earth metal with an inorganic or organic acid, or a compound which eliminates an alkali in heated condition. In particular, a hydroxide of alkaline metal and an alkaline metal salt of an inorganic or organic acid of weak or medium strength are listed. Among them, a hydroxide of sodium or potassium, a sodium salt and potassium salt are preferred. Specific examples of such acid bonding agents include sodium hydroxide, potassium hydroxide, sodium hydrogen carbonate, sodium carbonate, sodium formate, potassium carbonate, sodium primary, secondary or tertiary phosphate, sodium silicate and sodium trichloroacetate.

Dyeing of synthetic or natural polyamide and polyurethane fiber can be conducted by firstly exhausting a dye onto fiber from an acidic or weak acidic dye bath under controling pH, followed by changing pH value to neutral or alkaline range for fixing. Dyeing can be usually conducted at a temperature from 60 to 120° C. To attain satisfactory levelness, there can also be used a usual leveling agent, such as a condensation product of cyanuric chloride with aminobenzenesulfonic acid or aminonaphthakenesulfonic acid in an amount of 3-times by mol, or an adduct of stearylamine with ethylene oxide.

The monoazo compound (1) of the present invention imparts itself orange to scarlet color tone on a fiber material. To obtain desired color other than orange to scarlet, the compound (1) may be mixed with other dye in an amount which does not impair features of the present invention. A dye to be mixed and used is not particularly restricted provided that it is a reactive dye. Examples thereof include dyes containing at least one group from sulfatoethylsulfonic group, vinylsulfonic group, monochlorotriazine group, monofluorotriazine group, triazine mononicotinate group, dicyclotriazine group, difluoropyrimidine group and trichloropyrimidine group; dyes commercially available under the trademarks of Sumifix, Sumifix Supra, Remazol, Levafix, Procion, Cibacon, Basilen, Drimarene, Kaya cion, Kayacelon and the like, further, dyes described in JP-A-50-178, 51-17,538, 56-9,483, 56-15,481, 56-118,976, 56-128,380, 57-2,3657, 57-89,679, 57-143,360, 58-191,755, 59-15,451, 59-96,174, 59-161,463, 60-6,754, 60-123,559 60-229,957, 60-260,654, 61-126,175, 61-155,469, 61-225,256, 63-77, 974, 63-225,664, 1-185,370, 3-770, 5-247,366 and 6-287, 463, and dye represented by C. I. Reactive Blue 19 and C. I. Reactive Black 5.

The monoazo compound (1) of the present invention manifests excellent ability in dyeing and printing on a fiber material. It is particularly suitable for dyeing and printing of a cellulose fiber material, and a dyed material and a printed material obtained by using this compound have excellent light fastness, perspiration and light fastness, wet fastness such as washing fastness, peroxide washing fastness, chlorine fastness, perspiration fastness, acid hydrolysis fastness and alkali fastness, and further excellent abrasion fastness and iron fastness.

The monoazo compound (1) of the present invention is characterized by excellent dyeing ability, build-up property, level dyeing property and washing off property, excellent solubility and exhaustion and fixing property. Particularly, it is characterized by excellent dyeing and fixing property in deep color, and further, excellent low salt dyeing property. The compound (1) is also characterized in that it is not easily affected by variations in the dyeing temperature, the amounts of dyeing aids such as a salt and alkaline agent and bath ratio, and provides a dyed material having stable quality.

It is also characteristic feature of the present compound that the resulting dyed material is little suffered from discoloration in fixing treatment and resin finishing and does not reveal much change by contact with a basic substance during storage.

The intermediate compounds (A) and (B) of the present invention are useful as an intermediate for producing a fiber-reactive compound, such as a diazo component intermediate for a monoazo or polyazo compound, and are particularly useful as an intermediate for producing the monoazo compound (1) of the present invention.

The following examples further illustrate the present invention in detail, but should not be interpreted to limit the scope thereof. In the examples, all darts are by weight.

EXAMPLE 1

69.6 Parts of 4-methoxy-5-[4-(2-ethylanilino)-6-{3-(2-sulfateethylsulfonyl)anilino}-1,3,5-triazin-2 -ylamino] aniline-2-sulfonic acid was diazotized according to a usual method, and then, coupled with 28.1 parts by weight of 1-hydroxy-6-acetylaminonaphthalene-3-sulfonic acid according to a usual method. Thereafter, salting out was conducted to obtain a monoazo compound of which free acid is represented by the following formula.

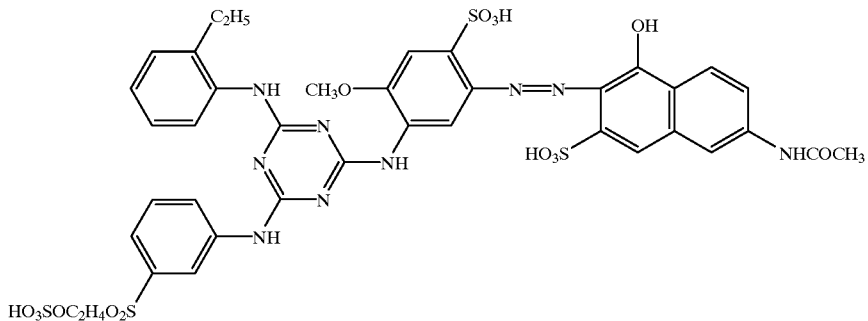

λmax=502 nm (in an aqueous medium)

EXAMPLE 2

The same synthesis procedure as in Example 1 was conducted using compounds shown in B column and C column in the following tables 1–10 instead of 4-methoxy-5-[4-(2-ethylanilino)-6-{3-(2-sulfateethylsulfonyl)anilino}-1,3,5-triazin-2-ylamino]aniline-2-sulfonic acid and 1-hydroxy-6-acetylaminonaphthalene-3-sulfonic acid to obtain corresponding monoazo compounds. Using one of the monoazo compounds thus obtained, dyeing was conducted to obtain a dyed material having a color tone shown in D column of the following tables 1–10.

TABLE 1

| A | B | C | D |
|---|---|---|---|
| 1 | (structure with HO₃SC₂H₄NH-triazine-NH-C₆H₄-SO₂C₂H₄SO₃H and CH₃O, NH₂, SO₃H substituents) | 5-hydroxy-7-sulfo-2-(acetylamino)naphthalene (OH, HO₃S, NHCOCH₃) | Scarlet |
| 2 | (triazine structure with CH₃, NH₂, SO₃H and two HO₃S-C₆H₄-NH groups, one bearing SO₂C₂H₄SO₃H) | 5-hydroxy-7-sulfo-2-(phenoxyamino)naphthalene (OH, HO₃S, NHCO-C₆H₅) | Scarlet |
| 3 | (triazine structure with CH₃O, NH₂, SO₃H, HO₃SOC₂H₄O₂S-C₂H₄-NH and HO₃S-C₆H₄-NH groups) | 5-hydroxy-7-sulfo-2-(maleamino)naphthalene (OH, HO₃S, NHCOCH=CHCO₂H) | Scarlet |
| 4 | (triazine with N(CH₃)₂, CH₃O, NH₂, SO₃H, ClC₂H₄O₂S-C₂H₄-NH and HO₃SOC₂H₄O₂S-C₆H₄-NH groups) | 5-hydroxy-7-sulfo-1-sulfo-2-(propionylamino)naphthalene (OH, HO₃S, SO₃H, NHCOC₂H₅) | Scarlet |

TABLE 1-continued

| A | B | C | D |
|---|---|---|---|
| 5 | ![structure with triazine linking pyridinium-carboxyphenyl, sulfoethylsulfonyl-phenylamino, and methyl-sulfo-amino-phenylamino groups] | ![naphthalene with OH, SO3H, and NHCOCH2CH2CO2H substituents] | Scarlet |

TABLE 2

| A | B | C | D |
|---|---|---|---|
| 6 | (triazine with morpholine, HO₃SOC₂H₄O₂S-phenyl-NH, and 2-amino-5-(NH)-benzenesulfonic acid substituents) | 8-hydroxy-3-sulfo-6-(NHCOCH₃)-naphthalene | Scarlet |
| 7 | (triazine with HO₃S-phenyl-NH, CH₂=CHSO₂-phenyl-NH, and 2-amino-5-(NH)-benzenesulfonic acid substituents) | 8-hydroxy-3-sulfo-6-(NHCO-phenyl)-naphthalene | Scarlet |
| 8 | (pyrimidine with CH₃O, HO₃SOC₂H₄S-C₂H₄-NH, and 2-amino-5-(NH)-benzenesulfonic acid substituents) | 8-hydroxy-3-sulfo-6-(NHCOCH=CHCO₂H)-naphthalene | Scarlet |
| 9 | (pyrimidine with HO₃SOC₂H₄O₂S-C₃H₆-NH, HO₃SOC₂H₄O₂S-phenyl-NH, and 2-amino-5-(NH)-benzenesulfonic acid substituents) | 8-hydroxy-3-sulfo-6-(NHCOC₂H₅)-naphthalene | Scarlet |

TABLE 2-continued

| A | B | C | D |
|---|---|---|---|
| 10 | (structure) | (structure) | Scarlet |

TABLE 3

| A | B | C | D |
|---|---|---|---|
| 11 | (structure) | (structure) | Scarlet |
| 12 | (structure) | (structure) | Scarlet |
| 13 | (structure) | (structure) | Scarlet |
| 14 | (structure) | (structure) | Scarlet |

TABLE 3-continued
| A | B | C | D |
|---|---|---|---|
| 15 | 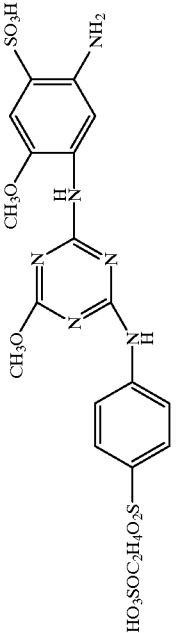 |  | Scarlet |

TABLE 4

| A | B | C | D |
|---|---|---|---|
| 16 | (structure) | (structure) | Scarlet |
| 17 | (structure) | (structure) | Scarlet |
| 18 | (structure) | (structure) | Scarlet |
| 19 | (structure) | (structure) | Scarlet |

TABLE 4-continued

| A | B | C | D |
|---|---|---|---|
| 20 | (structure with triazine bearing H₂NOC-pyridinium⁺, NH-aryl with SO₃H, CH₃, NH₂ substituents, and N(CH₃)-C₆H₄-SO₂C₂H₄OSO₃H) | (1-hydroxy-naphthalene-disulfonic acid linked via NH to triazine substituted with HN—CH₂CH₂SO₃H and NH—C₂H₄—SO₂C₂H₄Cl) | Scarlet |

TABLE 5

| A | B | C | D |
|---|---|---|---|
| 21 | (structure) | (structure) | Scarlet |
| 22 | (structure) | (structure) | Scarlet |
| 23 | (structure) | (structure) | Scarlet |
| 24 | (structure) | (structure) | Scarlet |

TABLE 5-continued

| A | B | C | D |
|---|---|---|---|
| 25 | HO₃SC₂H₄NH-[triazine]-NH-C₆H₄(SO₃H)(NH₂), with -NH-C₆H₄-SO₂C₂H₄OSO₃H substituent | [triazine linked to p-methoxyanilino, p-(SO₂C₂H₄OSO₃H)anilino, and N(CH₃)-naphthyl(OH)(SO₃H)] | Scarlet |

TABLE 6

| A | B | C | D |
|---|---|---|---|
| 26 | | | Scarlet |
| 27 | | | Scarlet |
| 28 | | | Scarlet |
| 29 | | | Scarlet |

TABLE 6-continued

| A | B | C | D |
|---|---|---|---|
| 30 | (structure: triazine with N+-pyridinium bearing H₂NOC, N(CH₃)-phenyl-SO₂C₂H₄OSO₃H, and NH-phenyl bearing SO₃H and NH₂) | (structure: 1-hydroxy-naphthalene-3,8-disulfonic acid linked via NH to a dichlorotriazine substituted with NH-C₂H₄-SO₂C₂H₄Cl) | Scarlet |

TABLE 7

| A | B | C | D |
|---|---|---|---|
| 31 | HO₃SOC₂H₄SO₂—(CH₂)₃O— (phenyl with SO₃H and NH₂) | Naphthalene(OH, SO₃H)-NH-triazine(Cl)-N(C₂H₅)-phenyl-SO₂C₂H₄OSO₃H | Scarlet |
| 32 | " | Naphthalene(OH, SO₃H)-NH-triazine-NH-phenyl(SO₃H), with NH-C₂H₄-SO₂CH=CH₂ | Scarlet |
| 33 | " | Naphthalene(OH, SO₃H)-NH-pyrimidine-NH-phenyl, with NH-C₂H₄-SO₂C₂H₄OSO₃H | Scarlet |
| 34 | " | Naphthalene(OH, SO₃H)-NH-triazine(Cl)-NH-C₂H₄-SO₂C₂H₄OSO₃H | Scarlet |

TABLE 7-continued
| A | B | C | D |
|---|---|---|---|
| 35 | " |  | Scarlet |

TABLE 8

| A | B | C | D |
|---|---|---|---|
| 36 | 2-amino-5-(HO$_3$SOC$_2$H$_4$SO$_2$)-benzenesulfonic acid (with SO$_3$H, NH$_2$) | Naphthol (OH, HO$_3$S-) linked via NH to triazine bearing HN—C$_2$H$_4$—SO$_2$C$_2$H$_4$OSO$_3$H and NH-C$_6$H$_4$-SO$_2$C$_2$H$_4$OSO$_3$H | Scarlet |
| 37 | 2-amino-5-(ClC$_2$H$_4$SO$_2$)-benzenesulfonic acid | Naphthol (OH, HO$_3$S-) linked via NH to fluorotriazine bearing HN—C$_6$H$_4$-SO$_3$H | Scarlet |
| 38 | 2-amino-5-(CH$_2$=CHSO$_2$)-benzenesulfonic acid | Naphthol (OH, HO$_3$S-, SO$_3$H) linked via NH to chlorotriazine bearing NH-C$_6$H$_4$-SO$_2$C$_2$H$_4$OSO$_3$H | Scarlet |
| 39 | 2-amino-5-(HO$_3$SOC$_2$H$_4$SO$_2$)-benzenesulfonic acid | Naphthol (OH, HO$_3$S-) linked via NH to triazine bearing NH—C$_2$H$_4$—SO$_2$C$_2$H$_4$OSO$_3$H and N-pyridinium-CO$_2$H | Scarlet |

TABLE 8-continued

| A | B | C | D |
|---|---|---|---|
| 40 | HO$_3$SOC$_2$H$_4$SO$_2$—(CH$_2$)$_3$O—[benzene with SO$_3$H, NH$_2$] | [naphthalene with OH, HO$_3$S, NH-linked to triazine with F, and N(CH$_3$)—C$_2$H$_4$—SO$_2$C$_2$H$_4$OSO$_3$H] | Scarlet |

TABLE 9

| A | B | C | D |
|---|---|---|---|
| 41 | (structure) | (structure) | Scarlet |
| 42 | (structure) | (structure) | Scarlet |
| 43 | (structure) | (structure) | Scarlet |
| 44 | (structure) | (structure) | Scarlet |

TABLE 9-continued

| A | B | C | D |
|---|---|---|---|
| 45 | HO₃SOC₂H₄SO₂·C₂H₄—NH—C(=O)—NH—C₂H₄—O— attached to benzene ring bearing SO₃H and NH₂ | Naphthalene bearing OH, HO₃S, and NH-linked to chlorotriazine with N(C₂H₅)-phenyl-SO₂C₂H₄OSO₃H | Scarlet |

TABLE 10

| A | B | C | D |
|---|---|---|---|
| 46 | HO₃SOC₂H₄SO₂—(CH₂)₃O— [2-amino-5-yl benzenesulfonic acid] | [4-hydroxy-7-(acetylamino)-2-naphthalenesulfonic acid] | Scarlet |
| 47 | CH₂=CHSO₂—(CH₂)₃O— [2-amino-5-yl benzenesulfonic acid] | [4-hydroxy-7-(NHCOC₂H₄CO₂H)-2-naphthalenesulfonic acid] | Scarlet |
| 48 | HO₃SOC₂H₄SO₂—C₂H₄OC₂H₄—O— [2-amino-5-yl benzenesulfonic acid] | [4-hydroxy-6-(NH-CO-C₆H₄-NHCOCH₃)-2-naphthalenesulfonic acid] | Scarlet |
| 49 | HO₃SOC₂H₄SO₂·C₂H₄—NH—C(O)—NH—C₂H₄—O— [4-amino-3-yl benzenesulfonic acid] | [4-hydroxy-7-(NH- with 5-chloro-2,6-difluoropyrimidin-4-yl)-2-naphthalenesulfonic acid] | Scarlet |
| 50 | HO₃SOC₂H₄SO₂—(CH₂)₃O— [2-amino-5-yl benzenesulfonic acid] | [4-hydroxy-7-(NH—CO—C₆H₄—NH-(5-chloro-2,6-difluoropyrimidin-4-yl))-2-naphthalenesulfonic acid] | Scarlet |

DYEING EXAMPLE 1

Each of the monoazo compounds obtained in Examples 1 and 2 (respectively 0.3 parts) was respectively dissolved in 200 parts of water. To the solution, 20 parts of sodium sulfate was added, and further 10 parts of cotton was added, and the solution was heated to 60° C. Thirty minutes after reaching to 60° C., 4 parts of sodium carbonate was added, and dyeing was conducted at the same temperature for 1 hour. After completion of the dyeing, water-washing and soaping were conducted to obtain a deep colored orange to scarlet dyed materials which is excellent in various fastness and has excellent build-up property.

DYEING EXAMPLE 2

The same dyeing procedure was conducted as in Dyeing Example 1 except that the amount of sodium salfate was changed from 20 parts to 10 parts to obtain a dyed material having the same qualities as in Dyeing Example 1 for each of monoazo compounds.

DYEING EXAMPLE 3

The same dyeing procedure was conducted as in Dyeing Example 1 except that the amount used of sodium sulfate was changed from 20 parts to 4 parts to obtain a dyed material having the same qualities as in Dyeing Example 1 for each of monoazo compounds.

DYEING EXAMPLE 4

The same dyeing procedure was conducted as in Dyeing Examples 1 to 3 except that the temperature was changed from 60° C. to 70 to obtain a dyed material having the same qualities as in Dyeing Example 1 for each of monoazo compounds.

DYEING EXAMPLE 5

The same dyeing procedure was conducted as in Dyeing Examples 1 to 3 except that the temperature was changed from 60° C. to 80° C. to obtain a dyed material having the same qualities as in Dyeing Example 1 for each of monoazo compounds.

DYEING EXAMPLE 6

Color pastes each having the following composition were prepared using each of the monoazo compounds obtained in Examples 1 and 2.

| Color paste composition | |
|---|---|
| Monoazo compound | 5 parts |
| Urea | 5 parts |
| Sodium alginate (5%) base paste | 50 parts |
| Boiling water | 25 parts |
| Sodium hydrogen carbonate | 2 parts |
| Balance (water) | 13 parts |

These color paste were printed on mercerized cotton broad cloth. After intermediate drying, steaming was conducted at 100° C. for 5 minutes. Then, washing with hot water, soaping, washing with hot water and drying were conducted to obtain an orange to scarlet printed material excellent in various fastness.

What is claimed is:

1. A monoazo compound represented by the following general formula (1) or a salt thereof:

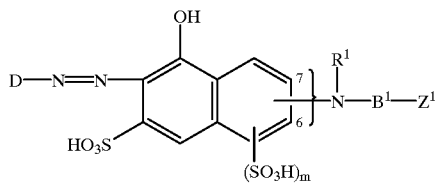

wherein m represents 0 or 1, $R^1$ represents a hydrogen atom or a lower alkyl group which may be optionally substituted, D represents a group represented by the following general formula (2a), (2b) or (2c):

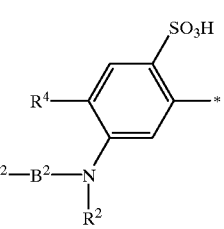

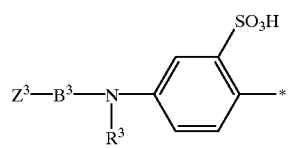

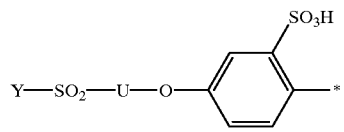

wherein $R^2$ and $R^3$ each independently represent a hydrogen atom or a lower alkyl group which may be optionally substituted, $R^4$ represents methyl or methoxy, U represents an alkylene which may be optionally interrupted by amino, carbamoyl, ureido or an oxygen atom, and * indicates a bond to an azo group, $B^1$, $B^2$ and $B^3$ each independently represent a direct bond or a connecting group represented by the following general formula (3):

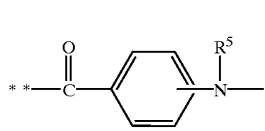

wherein, $R^5$ represents a hydrogen atom or a lower alkyl group which may be optionally substituted, ** indicates a bond to —$NR^1$—, —$NR^2$— or —$NR^3$—, $Z^1$ represents an alkylcarbonyl group which may be optionally substituted or a phenylcarbonyl group which may be optionally substituted, or a group represented by the following general formula (4a) or (4b), and $Z^2$ and $Z^3$ each independently represent a group represented by the following general formula (4a):

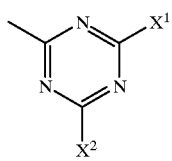
(4a)

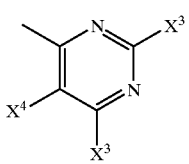
(4b)

wherein, both $X^1$ and $X^2$ represent chloro, or $X^1$ represents fluoro, chloro, pyridinio group which may be optionally substituted, or a group represented by the following formula (5a):

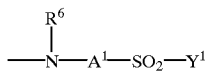
(5a)

and $X^2$ represents a group represented by the following general formula (5b), (5c), (5d) or (5e):

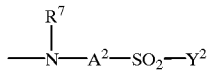
(5b)

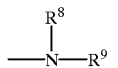
(5c)

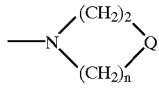
(5d)

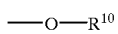
(5e)

wherein, $A^1$ and $A^2$ each independently represent alkylene which may be optionally substituted, phenylene which may be optionally substituted or naphthylene which may be optionally substituted, $R^6$, $R^7$, $R^8$, $R^9$ and $R^{10}$ each independently represent a hydrogen atom, alkyl which may be optionally substituted or phenyl which may be optionally substituted, Q represents —$CH_2$—, —O—, —S—, —$SO_2$— or —$NR^{11}$— wherein $R^{11}$ represents a hydrogen atom or alkyl which may be optionally substituted, n is 1, 2 or 3, $X^3$ represents fluoro or chloro, $X^4$ represents chloro, hydrogen atom, methyl or cyano, Y, $Y^1$ and $Y^2$ each independently represent —CH=$CH_2$ or —$CH_2CH_2L$ wherein L represents a group which is eliminatable by the action of alkali, and a group represented by —$NR^1$ is linked to 6-position or 7-position of the naphthalene ring;

provided that, when D represents a group of the formula (2a) or (2b) and $B^1$, $B^2$ and $B^3$ represent a direct bond, and $Z^1$, $Z^2$ and $Z^3$ each a group represented by the following general formula (4a), then, the general formula (4a) represents a group represented by the following general formula (4a-1) or (4a-2):

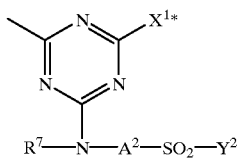
(4a-1)

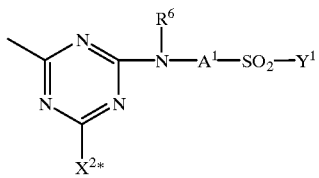
(4a-2)

wherein, $A^1$, $A^2$, $R^6$, $R^7$, $X^2$, $Y^1$ and $Y^2$ are as defined above, $X^{1*}$ represents fluoro or chloro, $X^{2*}$ represents a group represented by the general formula (5b), (5c), (5d) or (5e) or a pyridinio group which may be optionally substituted, and $Z^1$ and $Z^2$ do not simultaneously represent the general formula (4a-1) and $Z^1$ and $Z^3$ do not simultaneously represent the general formula (4a-1);

and when D represents a group of the formula (2a) or (2b), $B^2$ and $B^3$ represent a direct bond, $Z^1$ represents an alkylcarbonyl group which may be optionally substituted or a phenylcarbonyl group which may be optionally substituted and $B^1$ represents a direct bond, then $Z^2$ and $Z^3$ represent a group represented by the general formula (4a-2).

2. The monoazo compound or a salt thereof according to claim 1, wherein $B^1$ represents a direct bond.

3. The monoazo compound or a salt thereof according to claim 1, wherein $Z^1$ represents a group represented by the general formula (4a).

4. The monoazo compound or a salt thereof according to claim 1, wherein D represents a group represented by the general formula (2a) or (2b).

5. The monoazo compound or a salt thereof according to claim 4, wherein $B^2$ or $B^3$ represent a direct bond.

6. The monoazo compound or a salt thereof according to claim 4, wherein the group represented by the general formula (4a) is a group represented by the general formula (4a-2).

7. The monoazo compound or a salt thereof according to claim 1, wherein D represents a group represented by the general formula (2c).

8. The monoazo compound or a salt thereof according to claim 7, wherein U represents alkylene having 3 to 6 carbon atoms which may be optionally interrupted by an oxygen atom.

9. The monoazo compound or a salt thereof according to claim 1, wherein $X^1$ represents a fluoro, chloro or pyridinio group which may be optionally substituted, and $X^2$ represents a group represented by the general Formula (5b).

10. The monoazo compound or a salt thereof according to claim 1, wherein $X^1$ represents a group represented by the general formula (5a), and $X^2$ represents a group represented by the general formula (5b) or a group represented by the general formula (5c).

11. The monoazo compound or a salt thereof according to claim 1, wherein $A^1$ and $A^2$ each independently represent ethylene, trimethylene or phenylene which may be optionally substituted.

12. The monoazo compound or a salt thereof according to claim. 1, wherein at least one of Y, $Y^1$ and $Y^2$ represents —CH=CH$_2$, —CH$_2$CH$_2$Cl or —CH$_2$CH$_2$OSO$_3$H.

13. The monoazo compound or a salt thereof according to claim 1, wherein at least one of $R^1$, $R^2$, $R^3$, Rs, $R^6$ and $R^7$ represent hydrogen, methyl or ethyl.

14. A process for dyeing or printing a fiber material which comprises the step of contacting the monoazo compound or a salt thereof according to claim 1 with the fiber material.

* * * * *